US009031288B2

(12) United States Patent  (10) Patent No.: US 9,031,288 B2
Codella et al.  (45) Date of Patent: May 12, 2015

(54) UNIQUE CARDIOVASCULAR MEASUREMENTS FOR HUMAN IDENTIFICATION

(75) Inventors: Noel C. Codella, Lagrangeville, NY (US); Jonathan Connell, Cortlandt-Manor, NY (US); Gong Leiguang, New Brunswick, NJ (US); Apostol I. Natsev, Harrison, NY (US); Nalini Ratha, White Plains, NY (US)

(73) Assignee: International Business Machines Corporation, Armonk, NY (US)

( * ) Notice: Subject to any disclaimer, the term of this patent is extended or adjusted under 35 U.S.C. 154(b) by 473 days.

(21) Appl. No.: 13/449,720

(22) Filed: Apr. 18, 2012

(65) Prior Publication Data

US 2013/0279764 A1  Oct. 24, 2013

(51) Int. Cl.
*A61B 5/117* (2006.01)

(52) U.S. Cl.
CPC ........... *A61B 5/117* (2013.01); *A61B 2576/023* (2013.01)

(58) Field of Classification Search
None
See application file for complete search history.

(56) References Cited

U.S. PATENT DOCUMENTS

| 5,737,439 | A | 4/1998 | Lapsley et al. | |
| 6,993,378 | B2 | 1/2006 | Wiederhold et al. | |
| 7,956,890 | B2 | 6/2011 | Cheng et al. | |
| 8,031,912 | B2 | 10/2011 | Dennis et al. | |
| 2002/0138768 | A1 | 9/2002 | Murakami et al. | |
| 2008/0292169 | A1 | 11/2008 | Wang et al. | |
| 2008/0319275 | A1* | 12/2008 | Chiu et al. | 600/300 |
| 2009/0097713 | A1* | 4/2009 | DeLean | 382/115 |
| 2009/0262894 | A1* | 10/2009 | Shukla et al. | 378/65 |
| 2010/0113950 | A1 | 5/2010 | Lin et al. | |
| 2010/0145202 | A1 | 6/2010 | McLaughlin et al. | |
| 2010/0215238 | A1* | 8/2010 | Lu et al. | 382/131 |
| 2011/0064284 | A1* | 3/2011 | Punithakumar et al. | 382/128 |
| 2011/0209214 | A1 | 8/2011 | Simske et al. | |
| 2011/0211057 | A1* | 9/2011 | Iwase et al. | 348/78 |
| 2012/0173576 | A1* | 7/2012 | Gillam et al. | 707/780 |
| 2013/0039559 | A1* | 2/2013 | Grass et al. | 382/131 |
| 2013/0251099 | A1* | 9/2013 | Kunz et al. | 378/19 |
| 2013/0338447 | A1* | 12/2013 | Gilad-Gilor | 600/300 |

OTHER PUBLICATIONS

Cheng et al. ECG to Identify Individuals, Pattern Recognition, vol. 38, pp. 133-142, 2005.
Wubbeler et al. Verification of Humans Using the Electrocardiogram, Pattern Recogn. Lett., vol. 28, pp. 1172-1175, Jul. 2007.

(Continued)

*Primary Examiner* — Randolph I Chu
*Assistant Examiner* — Nathan Bloom
(74) *Attorney, Agent, or Firm* — Ryan, Mason & Lewis, LLP

(57) ABSTRACT

A method, an apparatus and an article of manufacture for generating a cardiovascular measurement for individual identification. The method includes acquiring at least one depiction of cardiac anatomy from an individual, extracting at least one quantified representation of cardiac anatomy from the at least one depiction, defining at least one comparison technique between the at least one quantified representation of cardiac anatomy and at least one additional quantified representation of cardiac anatomy, and identifying the individual based on the at least one defined comparison technique.

24 Claims, 9 Drawing Sheets

(56) References Cited

OTHER PUBLICATIONS

Haghjoo et al. The Effects of Sedative Music, Arousal Music, and Silence on Electrocardiography Signals, Journal of Electrocardiology, vol. 44, pp. 396, 2011.

Dande et al. Takotsubo Cardiomyopathy Followed by Neurogenic Stunned Myocardium in the Same Patient: Gradations of the Same Disease, Cardiology, vol. 118, No. 3, 2011.

Janik et al. Effects of Papillary Muscles and Trabeculae on Left Ventricular Quantification: Increased Impact on Methodological Variability in Patients with Left Ventricular Hypertrophy, Hypertension, vol. 26, pp. 1677-1685, 2008.

Waterton et al. Magnetic Resonance (mr) Cine Imaging of the Human Heart, Br J. Radiol, vol. 58, No. 692, pp. 711-716, 1985.

Cham et al. Left Ventricle: Automated Segmentation by Using Myocardial Effusion Threshold Reduction and Intravoxel Computation at MR Imaging, Radiology, vol. 248, No. 3, pp. 1004-1012, 2008.

Wong et al. Rapid and Accurate Left Ventricular Chamber Quantification Using a Novel CMR Segmentation Algorithm: a Clinical Validation Study, J. Magn Reson Imaging, vol. 31, No. 4, pp. 845-853, 2010.

Codella et al. Improved Left Ventricular Quantification with Partial Voxel Interpolation, in Vivo and Necropsy Validation of a Novel Cardiac MRI Segmentation Algorithm, Circulation Cardiovascular Imaging, 2011.

Wang et al. Analysis of Human Electrocardiogram for Biometric Recognition, EURASIP J. Adv. Signal Proc. 2008.

Nasri et al., Using ECG as a Measure in Biometric Identification Systems, TIC-STH, 2009, IEEE, pp. 28-33.

Pereira-Coutinho et al., One-Lead ECG-Based Personal Identification Using Ziv-Merhav Cross Parsing, 2010 International Conference on Pattern Recognition, IEEE, pp. 3858-3861.

El-Bendary et al., HSAS: Heart Sound Authentication System, 2010 Second World Congress on Nature and Biologically Inspired Computing, Dec. 15-17, 2010, pp. 351-356.

Guernoun et al., Continuous Authentication by Electrocardiogram Data, TIC-STH, 2009, IEEE, pp. 40-42.

Lee et al., Automatic Left Ventricle Segmentation Using Iteractive Thresholding and an Active Contour Model with Adaptation on Short-Axis Cardiac MRI, IEEE Transactions on Biomedical Engineering, vol. 57, No. 4, Apr. 2010, pp. 905-913.

Yamada et al., Impact of Artificial Gummy Fingers on Fingerprint Systems, Proceedings of SPIE, Optical Security and Counterfeit Deterrence Techniques, vol. 8577, Oct. 2002.

Hatzinakos et al., HeartID: Cardiac Biometric Recognition, Fourth IEEE International Conference on Biometrics: Theory Applications and Systems, 2010, pp. 1-5.

Li et al., Robust ECG Biometrics by Fusing Temporal and Cepstral Information, International Conference on Pattern Recognition, 2010, IEEE, pp. 1326-1329.

\* cited by examiner

UNIQUE CARDIOVASCULAR MEASUREMENTS FOR HUMAN IDENTIFICATION

FIELD OF THE INVENTION

Embodiments of the invention generally relate to information technology, and, more particularly, to biometrics.

BACKGROUND

The demand for robust biometrics is high in today's security-conscious society. Known solutions include fingerprint identification, iris scanning, facial recognition, etc. However, drawbacks of known solutions include the fact that anatomies utilized in such approaches are external to the body and subject to corruption via intentional injury. For example, there have been instances, where artificial fingerprints have been used to circumvent biometric security systems. In other biometrics modalities, similar attacks are possible, such as face masks to hide identity, and designer iris lenses to fool iris recognition systems.

Other approaches suggest that electrocardiography (ECG or EKG) signals or acoustic heartbeats offer uniqueness, but theses items have less information content than images, such as short-axis cardiac magnetic resonance imaging (MRI) images, which directly sense the anatomical geometry. Also, cardiac EKG may have fewer unique identifying characteristics to quantify because it assesses electrical activity of the heart, which is one-dimensional (1D) in nature.

Accordingly, more secure biometrics are needed.

SUMMARY

In one aspect of the present invention, techniques for unique cardiovascular measurements for human identification are provided. An exemplary computer-implemented method for generating a cardiovascular measurement for individual identification can include steps of acquiring at least one depiction of cardiac anatomy from an individual, extracting at least one quantified representation of cardiac anatomy from the at least one depiction, defining at least one comparison technique between the at least one quantified representation of cardiac anatomy and at least one additional quantified representation of cardiac anatomy, and identifying the individual based on the at least one defined comparison technique.

Another aspect of the invention or elements thereof can be implemented in the form of an article of manufacture tangibly embodying computer readable instructions which, when implemented, cause a computer to carry out a plurality of method steps, as described herein. Furthermore, another aspect of the invention or elements thereof can be implemented in the form of an apparatus including a memory and at least one processor that is coupled to the memory and operative to perform noted method steps. Yet further, another aspect of the invention or elements thereof can be implemented in the form of means for carrying out the method steps described herein, or elements thereof; the means can include (i) hardware module(s), (ii) software module(s), or (iii) a combination of hardware and software modules; any of (i)-(iii) implement the specific techniques set forth herein, and the software modules are stored in a tangible computer-readable storage medium (or multiple such media).

These and other objects, features and advantages of the present invention will become apparent from the following detailed description of illustrative embodiments thereof, which is to be read in connection with the accompanying drawings.

DETAILED DESCRIPTION

As described herein, an aspect of the present invention includes unique cardiovascular measurements for human identification. At least one embodiment of the invention includes a novel biometric signature for human identification based on anatomically unique structures of the left ventricle of the heart. Additionally, an aspect of such an embodiment includes an algorithm that analyzes three primary anatomical structures of the left ventricle: the endocardium, myocardium, and papillary muscles. Further, a comparison of the analyses between probe and gallery images produces a similarity score that is used as the basis of the biometric signatures for identification and authentication.

Using direct anatomical measurements of the left ventricle eliminates the intra-individual electrical variability seen with ECG while preserving biometric uniqueness from a complex cardiac structure. Cardiac structure is macroscopic and can be imaged using existing technologies. For example, at least one embodiment of the invention uses cardiac magnetic resonance imaging (MRI). The rich structure of the left ventricle as captured by cardiac MRI, as shown in FIG. 1, exhibits unique anatomical characteristics across individuals.

Figure 1:
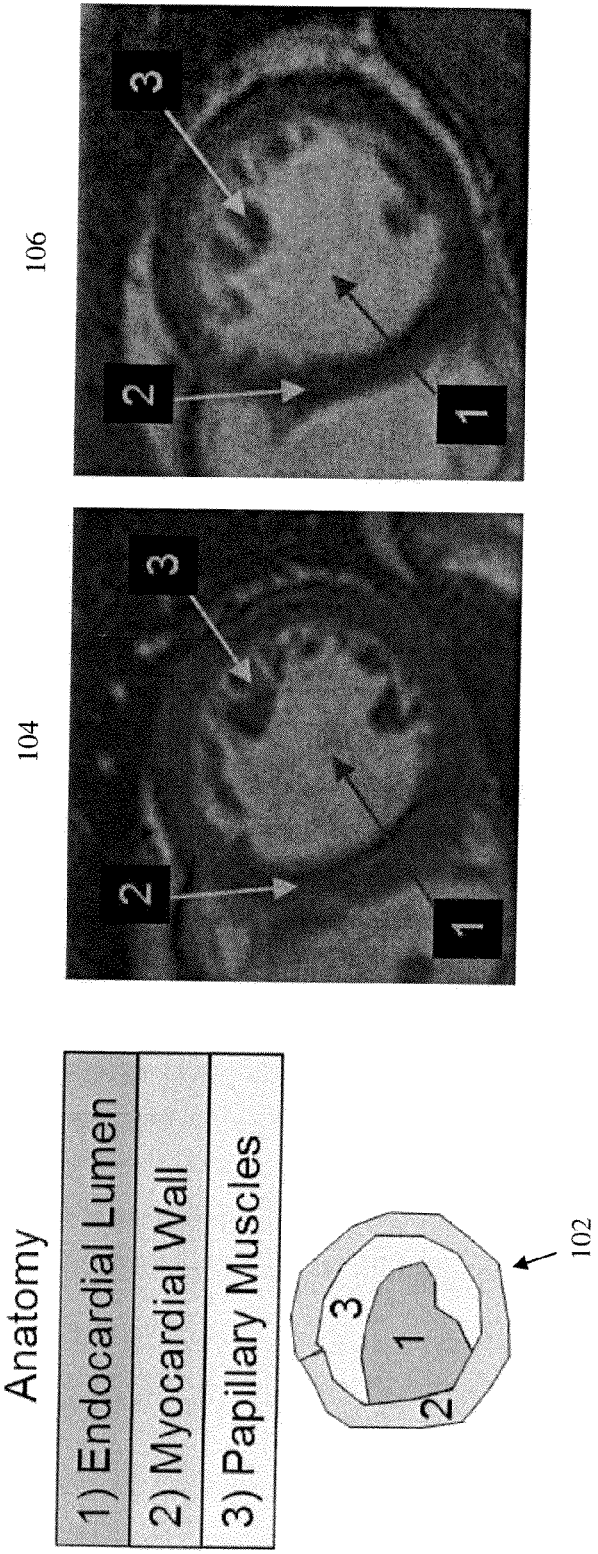
FIG. 1 is a diagram illustrating structure of example left ventricles as captured by cardiac MRI, according to an embodiment of the present invention.

FIG. 1 is a diagram illustrating structure of example left ventricles as captured by cardiac MRI, according to an embodiment of the present invention. By way of illustration, FIG. 1 depicts a drawn image of a left ventricle 102, as well as a cardiac MRI image 104 of a left ventricle captured from a first individual and a cardiac MRI image 106 of a left ventricle captured from a second individual. Also, as denoted in the index, images depicted in FIG. 1 illustrate anatomical elements of an endocardial lumen (1), a myocardial wall (2), and papillary muscles (3).

As illustrated, the left ventricular (LV) cavity of the heart contains structures know as "papillary" and "trabecular" muscles (PTM). These muscles are long, shaped similarly to strings or chords, and protrude out of the LV myocardial wall and up towards the base where the papillary muscles connect to the cusps of the valves via the chordae tendinae. The pattern of PTM and LV wall varies widely by individual. In one aspect of the invention, a quantification of the pattern of these muscles is implemented as a biometric marker.

As detailed herein, a biometric in accordance with an embodiment of the invention includes quantification of a set of measurements made through analysis of potentially multiple imaging modality signals such as, for example, MRI, computed tomography (CT), two-dimensional (2D) echo, three-dimensional (3D) echo, and positron emission tomography (PET), of the heart. In contrast to vulnerabilities of existing approaches, the heart is much less prone to corruption through intentional injury.

The left ventricle of the heart is currently imaged using the noted (and other) modalities, each of which may be acquired in multiple orientations. Two common imaging orientations include the long axis, which is parallel to the axis of the LV, and short axis, which is perpendicular to the long axis. Multiple short-axis images are typically acquired in order to image the entire volume of the LV. In at least one embodiment of the invention, quantification of the PTM and LV wall from images in these orientations is used as a unique signature for identification.

At least one embodiment of the invention can implement an algorithm with the following steps. LV segmentation can be carried out from base to apex (using, by way merely of example, a technique such as LV-METRIC). An additional step includes counting and characterizing PTM: extracting the location, size, and axis of each instance. Further, another step includes computing a kernel, or distance metric, between the features and measurements describing two left ventricles, that is invariant to scale and orientation along any of three axes. Such a computation may, in at least one embodiment of the invention, take into account similarity of PTM. This distance metric may also compute set difference and fiber similarity (cf. fingerprint minutiae).

As detailed herein, other variations of this algorithm may also be implemented in order to quantify measurements of the LV or other cardiac structures.

By way of merely illustration, example data collection can include the following steps, in accordance with an example embodiment of the invention. A short-axis cinematic steady state free-precession (Cine SSFP) MRI technique can be used to acquire cardiac image data from, for example, ten randomly selected de-identified subjects at two different times, corresponding to gallery enrollment and probe datasets. Cine SSFP images are acquired for multiple slice positions from left ventricular base to apex, and for multiple temporal phases along the cardiac cycle. In-plane image dimensions can include, for example, 34 centimeters (cm) by 34 cm, with six millimeter (mm) slice thickness, and four mm spacing between consecutive slices. The end diastolic phase (temporal phase where the left ventricle has filled with its maximal capacity of blood) can be selected, and three image slices that clearly depict the papillary structures in basal, mid-ventricular, and apical levels can be used as biometric signatures.

In order to facilitate a robust measure of similarity $S(p_x, g_y)$ between individual x in the probe dataset p, and individual y in the gallery dataset g, an algorithm in implemented in an aspect of the invention that performs an analysis of three anatomical features of the left ventricle: the endocardium, the myocardium, and the papillary muscles. Each analysis produces its own unique similarity score $S^E$, $S^M$, and $S^P$. The final similarity measure S is computed as the average:

$$S(p_x, g_y) = \frac{S^E(p_x, g_y) + S^M(p_x, g_y) + S^P(p_x, g_y)}{3} \quad (1)$$

Because there are ten individuals in this example, this produces a 10×10 similarity matrix. Each of the three analysis techniques as described herein.

The endocardial analysis can utilize, for example, a clinical segmentation technique named LV-METRIC, a soft-segmentation technique that computes the fractional content of blood and myocardium in each voxel comprising the left ventricle, which may be useful for capturing the anatomically complex structure of the endocardium.

Using the endocardial segmentation results, a measure is defined to quantify the anatomical similarity $S_{img}^E(p_{x,z}, g_{y,z})$ between any two cross-sectional images of the left ventricle:

$$S_{img}^E(p_{x,z}, g_{y,z}) = (1 - D_E(p_{x,z}, g_{y,z})) \quad (2)$$

where $p_{x,z}$ corresponds to the $z^{th}$ image of individual x in the probe dataset, and $g_{y,z}$ corresponds to the $z^{th}$ image of individual y in the gallery dataset. The $D_E$ image distance function is defined in representation 202 in FIG. 2.

Similarity between entire individuals $S^E(p_x, g_y)$ from the probe and gallery datasets is determined by taking the average similarity between each image-level pair-wise comparison:

$$S^E(p_x, g_y) = \frac{1}{N_z} \sum_{z=1}^{N_z} S_{img}^E(p_{x,z}, g_{y,z}) \quad (3)$$

where $N_z = 3$.

The myocardial analysis can be based, for example, on the LV-ITHACA clinical myocardial segmentation algorithm, which is an active contour model (ACM) technique initialized by the convex hull of the LV-METRIC results. Contour energy is iteratively minimized, defined by a combination of internal forces involving shape stiffness, and external forces involving edge and intensity information, relative to myocardial signal intensity estimated by LV-METRIC.

As in the case of the endocardial analysis, the similarity measure between images $S_{img}^M(p_{x,z}, g_{y,z})$ and similarities between individuals $S^M(p_x, g_y)$ are computed using Equations (2) and (3) detailed herein, respectively, replacing $D_E$ with $D_M$ in Eq. (2) as defined in representation 204 in FIG. 2, and $S_{img}^E$ with $S_{img}^M$ in Eq. (3).

Figure 2:
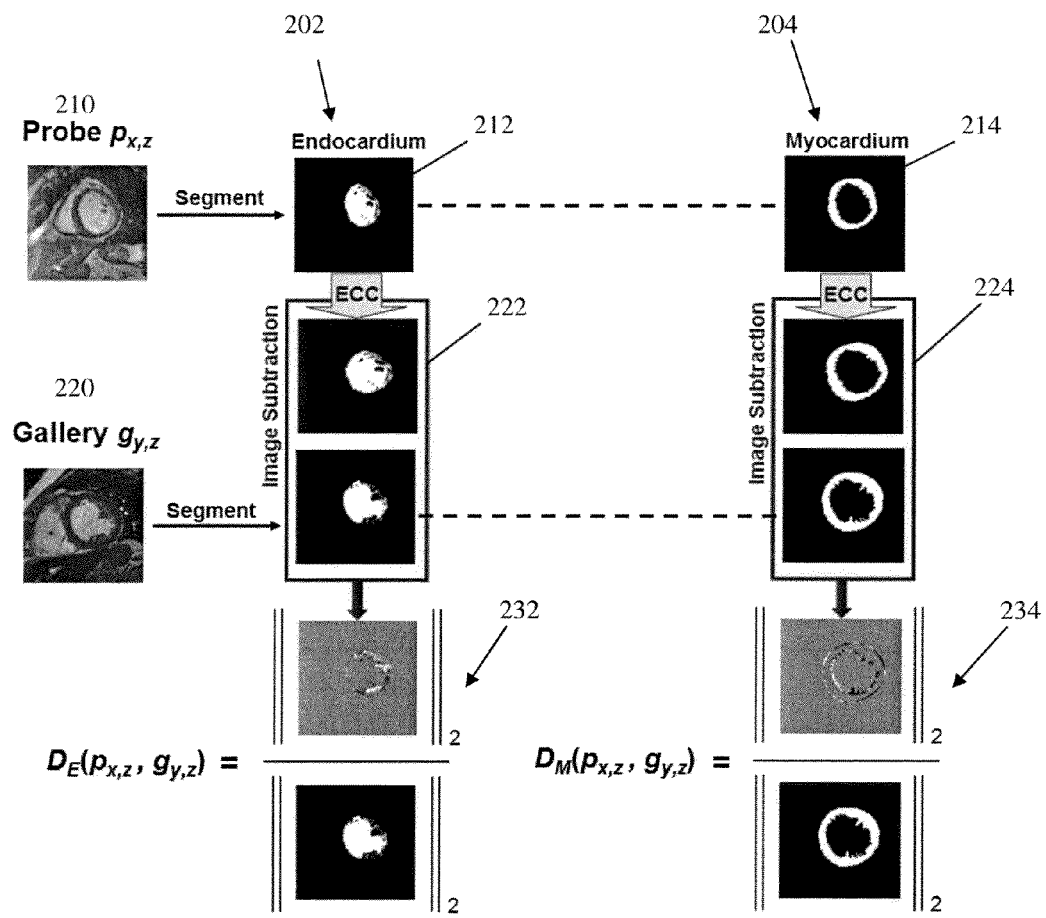
FIG. 2 is a diagram illustrating example endocardial and myocardial distance computations.

FIG. 2 is a diagram illustrating example endocardial 202 and myocardial 204 distance computations. Anatomical distances are computed by segmentation of both probe 210 and gallery 220 images, registration of the probe to the gallery segmentation (as represented by items 212 and 214), subtraction of the registered segmentations (as represented by items 222 and 224), and the L2-norm of the result scaled by the L2-norm of the gallery image (as represented by items 232 and 234).

As also detailed herein, the papillary analysis isolates discrete papillary muscles for the purposes of biometric matching. The analysis finds the left ventricle by enhancing contrast, thresholding the image, and selecting the region nearest the center. A centroid and ellipse are fitted to the left ventricular region and used to warp the ventricle to a circular shape. The image is rotated to a normalized orientation based on two points designating the center of the ventricle and the posterior end of the mid-ventricular septum. The point on the septum is located at the lower right corner of the right ventricle, which is detected as the first region to the left of the left ventricle. Further, the geometrically corrected image is again contrast enhanced.

Figure 3:
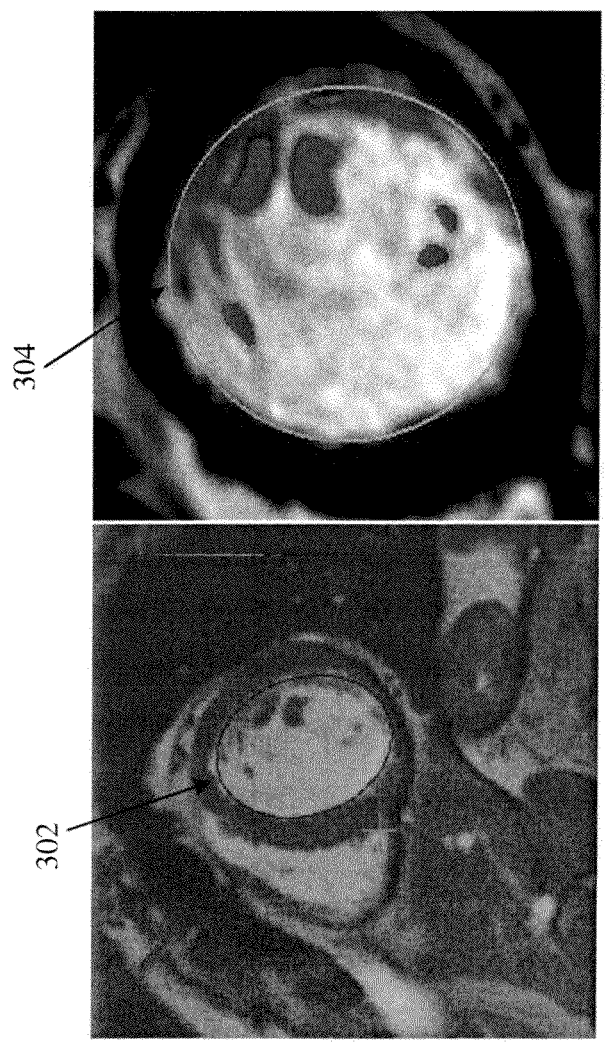
FIG. 3 is a diagram illustrating papillary muscle segmentation, according to an embodiment of the present invention.

FIG. 3 is a diagram illustrating cardiac images, according to an embodiment of the present invention. Specifically, FIG. 3 depicts a sample of the elliptical approximation and the localization of the septum (302) which is used to generate the normalized image (304). The warped circular approximation is shown as well.

The next step in the analysis includes extracting the papillary muscles by applying a center-surround operator to the normalized image to account for local brightness variations. The result is thresholded, and the regions that are either very small or occur outside of the left ventricle are removed. The remaining regions are again cleaned-up using morphological operations to yield discrete papillary muscles.

Figure 4:
FIG. 4 is a diagram illustrating papillary muscle distance computations, according to an embodiment of the present invention.

The pixel overlap of papillary muscle areas is then computed. FIG. 4 is a diagram illustrating cardiac images, according to an embodiment of the present invention. Specifically, FIG. 4 depicts two normalized images (402 and 404) with their detected papillary muscles, and the overlap of the papillary muscle pixels. A probe papillary muscle is considered to completely match (such as depicted in image 406) if it overlaps more than 50% with one or more papillary muscles in the gallery image.

The aggregated similarity between probe and gallery images is defined as:

$$S_{img}^{P}(p_{x,z}, g_{y,z}) = \frac{P_{matched}}{P_{total}} \quad (4)$$

where $P_{matched}$ is the total pixels in a image comprised of the union of all matched elements from the probe and gallery images, and $P_{matched}$ is the total pixels in an image comprised of the union of all elements (matched or unmatched) from the probe and gallery images. To compute similarity between entire individuals:

$$S^{P}(p_x, g_y) = \underset{z}{\mathrm{argmax}}\, S_{img}^{P}(p_{x,z}, g_{y,z}) \quad (5)$$

where z can take on values 1 through 3.

Accordingly, as detailed herein, at least one embodiment of the invention includes steps of acquiring representations of cardiac anatomy (via MRI, CT, echo, etc.), quantifying the representations using array of segmentation techniques, defining a similarity measure between representations, and identifying individuals based on similarity.

Figure 5:
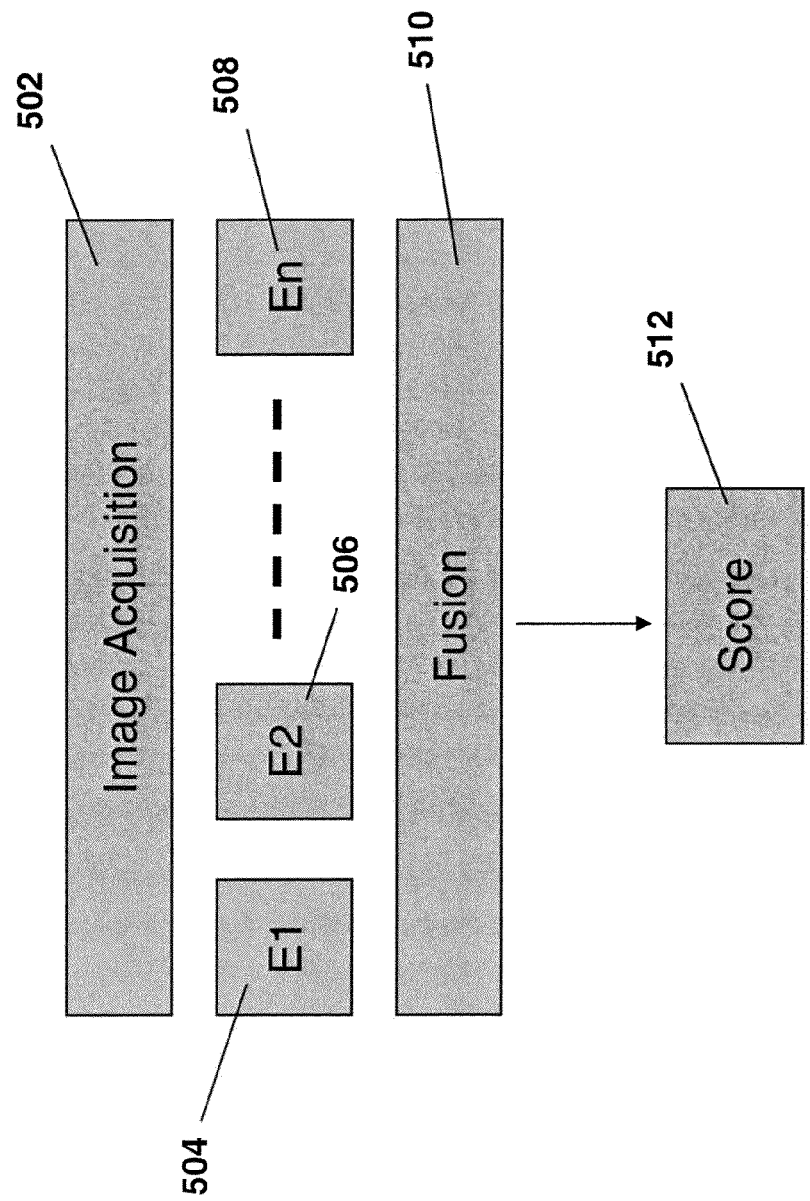
FIG. 5 is a diagram illustrating components, according to an embodiment of the present invention.

FIG. 5 is a diagram illustrating components, according to an embodiment of the present invention. By way of illustration, FIG. 5 depicts an image acquisition component 502, such as MRI, CT, Echo/Ultrasound or PET, first extraction of multiple quantified representations (E1) 504, second extraction (E2) 506, last extraction of quantified representation (En) 508, followed by a fusion component 510 that combines quantified representations into a unified representation, and a score 512.

Figure 6:
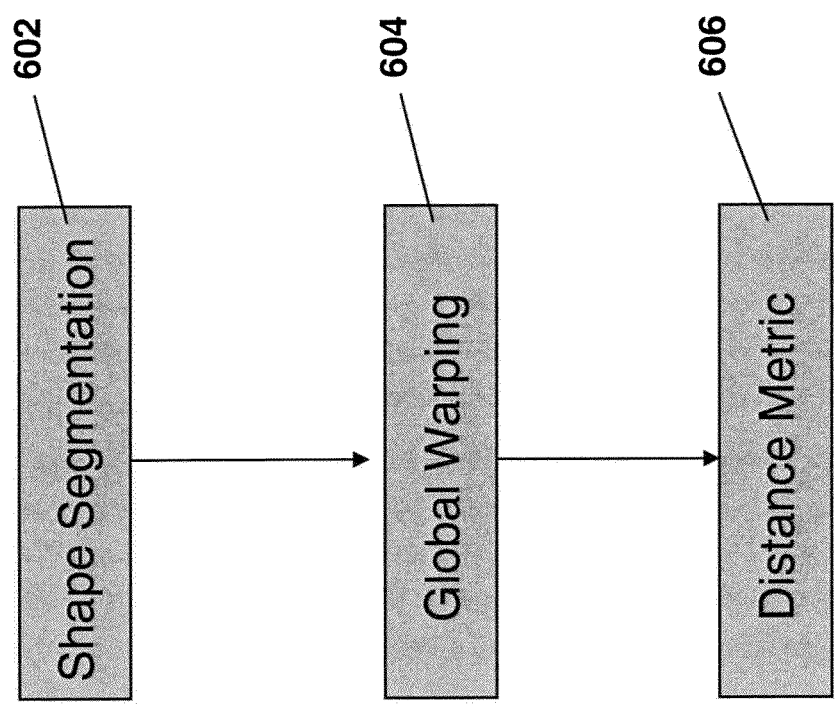
FIG. 6 is a diagram illustrating components, according to an embodiment of the invention.

FIG. 6 is a diagram illustrating components, according to an embodiment of the present invention. By way of illustration, FIG. 6 depicts a shape segmentation component 602, a global warping component 604 and a distance metric component 606. As an example of data flow, two depictions are first segmented. Their segmentations are aligned via global warping, and the two aligned segmentations are then compared to produce a score.

Figure 7:
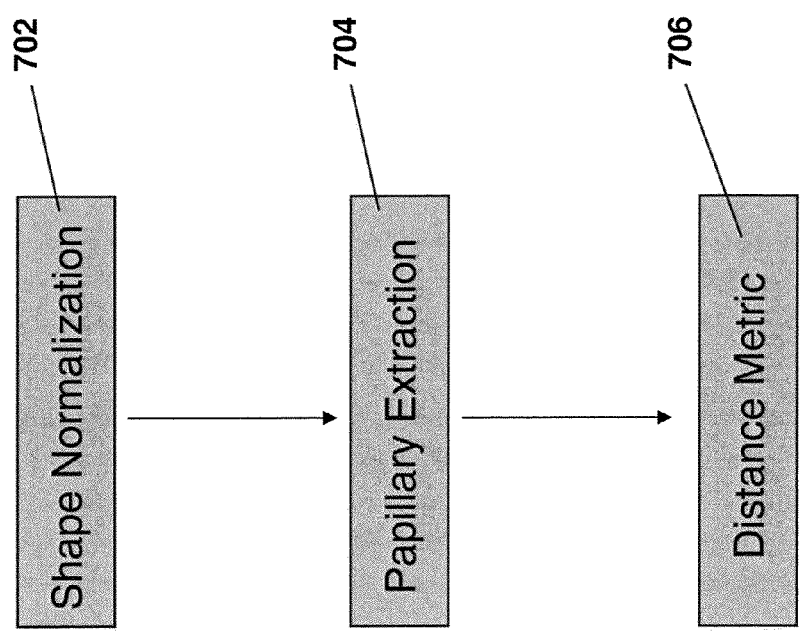
FIG. 7 is a diagram illustrating components, according to an embodiment of the invention.

FIG. 7 is a diagram illustrating components, according to an embodiment of the present invention. By way of illustration, FIG. 7 depicts a shape normalization component 702, a papillary extraction component 704 and a distance metric component 706. As an example of data flow, two depictions are first shape normalized. Their normalized shapes are then input into a method to extract quantified papillary structures. The papillary structures are then compared to produce a score.

Figure 8:
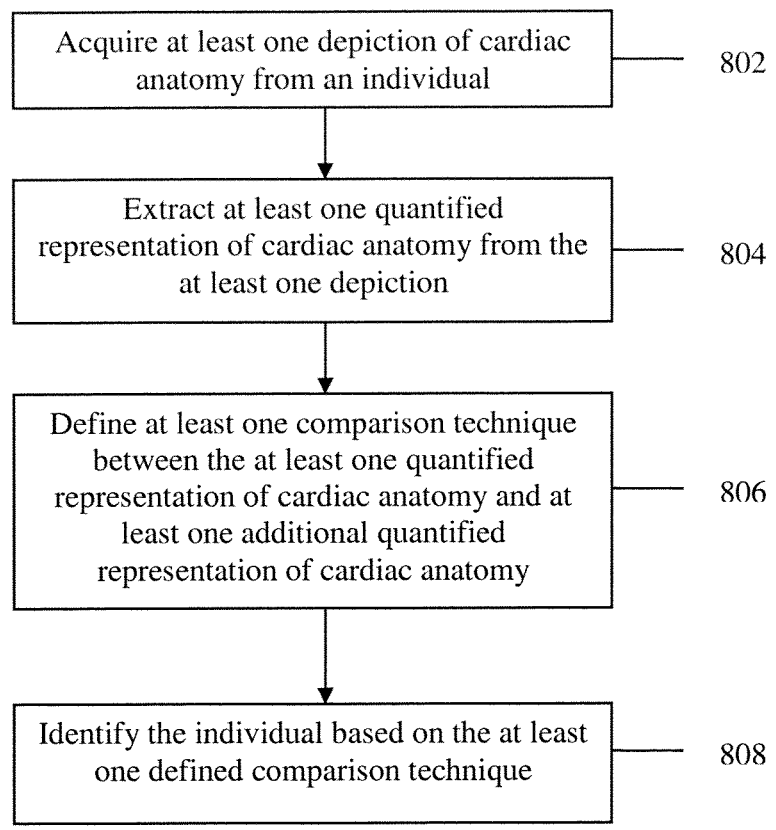
FIG. 8 is a flow diagram illustrating techniques for generating a cardiovascular measurement for individual identification, according to an embodiment of the invention.

FIG. 8 is a flow diagram illustrating techniques for generating a cardiovascular measurement for individual identification, according to an embodiment of the present invention. Step 802 includes acquiring at least one depiction of cardiac anatomy from an individual. As detailed herein, a depiction can include a digital image. In at least one embodiment of the invention, the cardiac anatomy includes a left ventricle of a heart. The depiction of cardiac anatomy from an individual can include a transverse slice of the left ventricle. Also, the depiction of cardiac anatomy can be acquired during end diastolic phase.

Additionally, as detailed herein, acquiring the at least one depiction of cardiac anatomy can include acquiring a depiction of cardiac anatomy via at least one anatomical imaging modality including one of magnetic resonance imaging (MRI), computed tomography (CT), two-dimensional (2D) echo/ultrasound, three-dimensional (3D) echo/ultrasound, positron emission tomography (PET) or a combination thereof.

Step 804 includes extracting at least one quantified representation of cardiac anatomy from the at least one depiction. Extracting at least one quantified representation of cardiac anatomy can include using a segmentation technique. Step 806 includes defining at least one comparison technique between the at least one quantified representation of cardiac anatomy and at least one additional quantified representation of cardiac anatomy. The comparison technique between the at least one quantified representation of cardiac anatomy and at least one additional quantified representation of cardiac anatomy can include implementing an algorithm that analyzes left ventricle anatomical structures including at least one of endocardium, myocardium, and papillary muscles.

Step 808 includes identifying the individual based on the at least one defined comparison technique. Identifying the individual based on the at least one defined comparison technique can include defining a similarity measure between the at least one quantified representation of cardiac anatomy from the individual and at least one additional quantified representation of cardiac anatomy to produce at least one score (that is used as the basis of a biometric). Comparing the quantified representation of cardiac anatomy from the individual and at least one additional quantified representation of cardiac anatomy includes geometric aligning and warping of the representations to be compared.

Further, in at least one embodiment of the invention, the at least one depiction of cardiac anatomy from an individual is a plurality of images for the individual, and comparing the quantified representations of cardiac anatomy from the individual and at least one additional quantified representation of cardiac anatomy includes computing a score between pairs of images from individuals, and generating a final comparison score which is a function of two or more pair scores. Additionally, comparing the quantified representation of cardiac anatomy from the individual and at least one additional quantified representation of cardiac anatomy is based on a pixel-wise difference of one or more selected anatomical structures in a representation. Comparing the quantified representation of cardiac anatomy from the individual and at least one additional quantified representation of cardiac anatomy can also be based on identifying individual papillary fibers and determining a correspondence between fibers in two representations.

Also, identifying the individual based on the at least one defined comparison technique can include defining two or more similarity measures between the at least one quantified representation of cardiac anatomy from the individual and at least one additional quantified representation of cardiac anatomy, and combining the two or more similarity measures to produce at least one score. Further, identifying the individual based on the defined similarity measure can also be based on a similarity measure threshold. The similarity measure threshold can be different for different individuals.

The techniques depicted in FIG. 8 can also, as described herein, include providing a system, wherein the system includes distinct software modules, each of the distinct software modules being embodied on a tangible computer-readable recordable storage medium. All the modules (or any subset thereof) can be on the same medium, or each can be on a different medium, for example. The modules can include any or all of the components shown in the figures. In an aspect of the invention, the modules can run, for example on a hardware processor. The method steps can then be carried out using the distinct software modules of the system, as described above, executing on a hardware processor. Further, a computer program product can include a tangible computer-readable recordable storage medium with code adapted to be executed to carry out at least one method step described herein, including the provision of the system with the distinct software modules.

Additionally, the techniques depicted in FIG. 8 can be implemented via a computer program product that can include computer useable program code that is stored in a computer readable storage medium in a data processing system, and wherein the computer useable program code was downloaded over a network from a remote data processing system. Also, in an aspect of the invention, the computer program product can include computer useable program code that is stored in a computer readable storage medium in a server data processing system, and wherein the computer useable program code is downloaded over a network to a remote data processing system for use in a computer readable storage medium with the remote system.

As will be appreciated by one skilled in the art, aspects of the present invention may be embodied as a system, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in a computer readable medium having computer readable program code embodied thereon.

An aspect of the invention or elements thereof can be implemented in the form of an apparatus including a memory and at least one processor that is coupled to the memory and operative to perform exemplary method steps.

Figure 9:
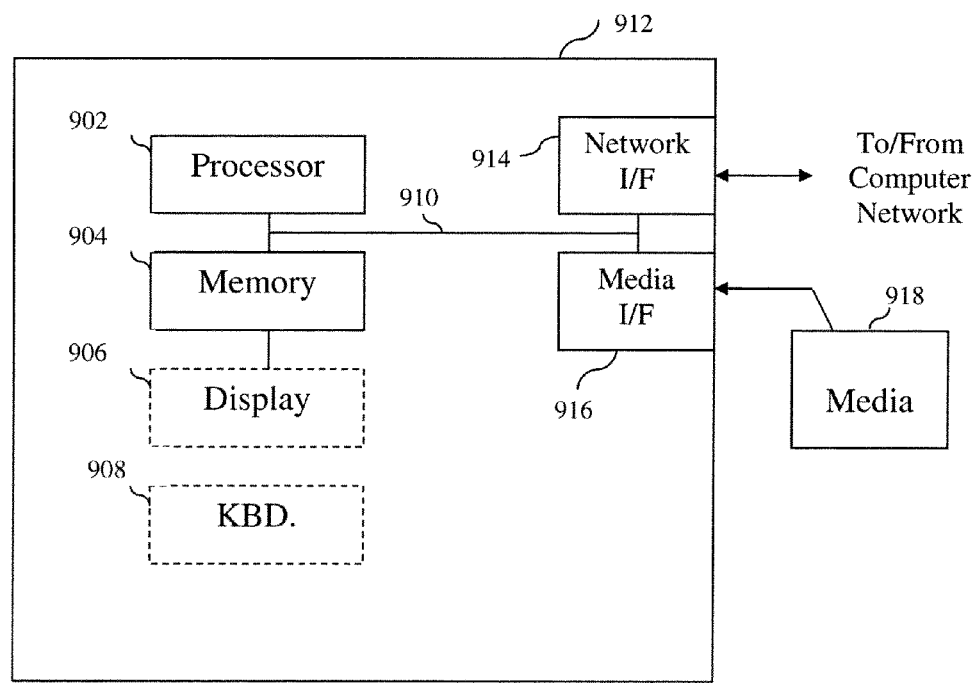
FIG. 9 is a system diagram of an exemplary computer system on which at least one embodiment of the invention can be implemented.

Additionally, an aspect of the present invention can make use of software running on a general purpose computer or workstation. With reference to FIG. 9, such an implementation might employ, for example, a processor 902, a memory 904, and an input/output interface formed, for example, by a display 906 and a keyboard 908. The term "processor" as used herein is intended to include any processing device, such as, for example, one that includes a CPU (central processing unit) and/or other forms of processing circuitry. Further, the term "processor" may refer to more than one individual processor. The term "memory" is intended to include memory associated with a processor or CPU, such as, for example, RAM (random access memory), ROM (read only memory), a fixed memory device (for example, hard drive), a removable memory device (for example, diskette), a flash memory and the like. In addition, the phrase "input/output interface" as used herein, is intended to include, for example, a mechanism for inputting data to the processing unit (for example, mouse), and a mechanism for providing results associated with the processing unit (for example, printer). The processor 902, memory 904, and input/output interface such as display 906 and keyboard 908 can be interconnected, for example, via bus 910 as part of a data processing unit 912. Suitable interconnections, for example via bus 910, can also be provided to a network interface 914, such as a network card, which can be provided to interface with a computer network, and to a media interface 916, such as a diskette or CD-ROM drive, which can be provided to interface with media 918.

Accordingly, computer software including instructions or code for performing the methodologies of the invention, as described herein, may be stored in an associated memory devices (for example, ROM, fixed or removable memory) and, when ready to be utilized, loaded in part or in whole (for example, into RAM) and implemented by a CPU. Such software could include, but is not limited to, firmware, resident software, microcode, and the like.

A data processing system suitable for storing and/or executing program code will include at least one processor 902 coupled directly or indirectly to memory elements 904 through a system bus 910. The memory elements can include local memory employed during actual implementation of the program code, bulk storage, and cache memories which provide temporary storage of at least some program code in order to reduce the number of times code must be retrieved from bulk storage during implementation.

Input/output or I/O devices (including but not limited to keyboards 908, displays 906, pointing devices, and the like) can be coupled to the system either directly (such as via bus 910) or through intervening I/O controllers (omitted for clarity).

Network adapters such as network interface 914 may also be coupled to the system to enable the data processing system to become coupled to other data processing systems or remote printers or storage devices through intervening private or public networks. Modems, cable modem and Ethernet cards are just a few of the currently available types of network adapters.

As used herein, including the claims, a "server" includes a physical data processing system (for example, system 912 as shown in FIG. 9) running a server program. It will be understood that such a physical server may or may not include a display and keyboard.

As noted, aspects of the present invention may take the form of a computer program product embodied in a computer readable medium having computer readable program code embodied thereon. Also, any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using an appropriate medium, including but not limited to wireless, wireline, optical fiber cable, RF, etc., or any suitable combination of the foregoing.

Computer program code for carrying out operations for aspects of the present invention may be written in any combination of at least one programming language, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described herein with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks. Accordingly, an aspect of the invention includes an article of manufacture tangibly embodying computer readable instructions which, when implemented, cause a computer to carry out a plurality of method steps as described herein.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

The flowchart and block diagrams in the figures illustrate the architecture, functionality, and operation of possible implementations of systems, methods and computer program products according to various embodiments of the present invention. In this regard, each block in the flowchart or block diagrams may represent a module, component, segment, or portion of code, which comprises at least one executable instruction for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

It should be noted that any of the methods described herein can include an additional step of providing a system comprising distinct software modules embodied on a computer readable storage medium; the modules can include, for example, any or all of the components detailed herein. The method steps can then be carried out using the distinct software modules and/or sub-modules of the system, as described above, executing on a hardware processor 902. Further, a computer program product can include a computer-readable storage medium with code adapted to be implemented to carry out at least one method step described herein, including the provision of the system with the distinct software modules.

In any case, it should be understood that the components illustrated herein may be implemented in various forms of hardware, software, or combinations thereof; for example, application specific integrated circuit(s) (ASICS), functional circuitry, an appropriately programmed general purpose digital computer with associated memory, and the like. Given the teachings of the invention provided herein, one of ordinary skill in the related art will be able to contemplate other implementations of the components of the invention.

The terminology used herein is for the purpose of describing particular embodiments only and is not intended to be limiting of the invention. As used herein, the singular forms "a," "an" and "the" are intended to include the plural forms as well, unless the context clearly indicates otherwise. It will be further understood that the terms "comprises" and/or "comprising," when used in this specification, specify the presence of stated features, integers, steps, operations, elements, and/ or components, but do not preclude the presence or addition of another feature, integer, step, operation, element, component, and/or group thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

At least one aspect of the present invention may provide a beneficial effect such as, for example, providing a new biometric using direct anatomical measurement of the left ventricle, which eliminates the intra-individual electrical variability seen with ECG, while preserving biometric uniqueness from complex cardiac structure.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A method for generating a cardiovascular measurement for individual identification, wherein the method comprises:
    acquiring multiple imaging modality signals pertaining to cardiac anatomy of a given individual, wherein the cardiac anatomy comprises a left ventricle of a heart;
    extracting multiple quantified representation of cardiac anatomy from the a multiple imaging modality signals, wherein the multiple quantified representations comprise (i) a quantified representation of an endocardial lumen of the left ventricle, (ii) a quantified representation of a myocardial wall of the left ventricle, and (iii) a quantified representation of papillary muscles of the left ventricle;
    determining a pattern of cardiac anatomy associated with the given individual based on (i) the quantified representation of the endocardial lumen of the left ventricle, (ii) the quantified representation of the myocardial wall of the left ventricle, and (iii) the quantified representation of the papillary muscles of the left ventricle;
    defining at least one comparison technique between the pattern of cardiac anatomy associated with the given individual and at least one additional pattern of cardiac anatomy; and
    identifying the given individual based on the at least one defined comparison technique.

2. The method of claim 1, wherein the multiple imaging modality signals comprises a transverse slice of the left ventricle.

3. The method of claim 1, wherein an imaging modality signal comprises a digital image.

4. The method of claim 1, wherein the multiple imaging modality signals pertaining to cardiac anatomy is acquired during end diastolic phase.

5. The method of claim 1, wherein acquiring the multiple imaging modality signals pertaining to cardiac anatomy comprises acquiring the multiple imaging modality signals pertaining to cardiac anatomy via at least one anatomical imaging modality including one of magnetic resonance imaging (MRI), computed tomography (CT), two-dimensional (2D) echo/ultrasound, three-dimensional (3D) echo/ultrasound, positron emission tomography (PET) or a combination thereof.

6. The method of claim 1, wherein identifying the given individual comprises defining a similarity measure between the pattern of cardiac anatomy associated with the given individual and at least one additional pattern of cardiac anatomy to produce at least one score.

7. The method of claim 6, wherein the pattern of cardiac anatomy associated with the given individual is a plurality of images for the given individual, and wherein said comparing comprises computing a score between pairs of images from individuals, and generating a final comparison score which is a function of two or more pair scores.

8. The method of claim 6, wherein identifying the given individual based on the defined similarity measure is based on a similarity measure threshold.

9. The method of claim 8, wherein the similarity measure threshold is different for different individuals.

10. The method of claim 1, wherein said defining at least one comparison technique comprises geometric aligning and warping of the representations to be compared.

11. The method of claim 1, wherein said defining at least one comparison technique is based on a pixel-wise difference of one or more selected anatomical structures in a representation.

12. The method of claim 1, wherein said defining at least one comparison technique is based on identifying individual papillary fibers and determining a correspondence between fibers in two representations.

13. The method of claim 1, wherein said extracting comprises using a segmentation technique.

14. The method of claim 1, wherein the at least one comparison technique comprises implementing an algorithm that analyzes left ventricle anatomical structures including at least one of endocardium, myocardium, and papillary muscles.

15. The method of claim 1, wherein identifying the given individual based on the at least one defined comparison technique comprises:
    defining two or more similarity measures between the pattern of cardiac anatomy associated with the given individual and at least one additional pattern of cardiac anatomy; and
    combining the two or more similarity measures to produce at least one score.

16. An article of manufacture comprising a non-transitory computer readable storage medium having computer readable instructions tangibly embodied thereon which, when implemented, cause a computer to carry out a plurality of method steps comprising:
    acquiring multiple imaging modality signals pertaining to cardiac anatomy of a given individual, wherein the cardiac anatomy comprises a left ventricle of a heart;
    extracting multiple quantified representation of cardiac anatomy from the multiple imaging modality signals, wherein the multiple quantified representations comprise (i) a quantified representation of an endocardial lumen of the left ventricle, (ii) a quantified representation of a myocardial wall of the left ventricle, and (iii) a quantified representation of papillary muscles of the left ventricle;

determining a pattern of cardiac anatomy associated with the given individual based on (i) the quantified representation of the endocardial lumen of the left ventricle, (ii) the quantified representation of the myocardial wall of the left ventricle, and (iii) the quantified representation of the papillary muscles of the left ventricle;

defining at least one comparison technique between the pattern of cardiac anatomy associated with the given individual and at least one additional pattern of cardiac anatomy; and identifying the given individual based on the at least one defined comparison technique.

17. The article of manufacture of claim 16, wherein said identifying the given individual based on the at least one defined comparison technique comprises defining a similarity measure between the pattern of cardiac anatomy associated with the given individual and at least one additional pattern of cardiac anatomy to produce at least one score.

18. The article of manufacture of claim 17, wherein comparing the pattern of cardiac anatomy associated with the given individual and at least one additional pattern of cardiac anatomy includes geometric aligning and warping of the representations to be compared.

19. The article of manufacture of claim 17, wherein comparing the pattern of cardiac anatomy associated with the given individual and at least one additional pattern of cardiac anatomy comprises identifying individual papillary fibers and determining a correspondence between fibers in two representations.

20. A system for generating a cardiovascular measurement for individual identification, comprising:

at least one distinct software module, each distinct software module being embodied on a tangible computer-readable medium;

a memory; and at least one processor coupled to the memory and operative for:

acquiring multiple imaging modality signals pertaining to cardiac anatomy of a given individual, wherein the cardiac anatomy comprises a left ventricle of a heart;

extracting multiple quantified representation of cardiac anatomy from the multiple imaging modality signals, wherein the multiple quantified representations comprise (i) a quantified representation of an endocardial lumen of the left ventricle, (ii) a quantified representation of a myocardial wall of the left ventricle, and (iii) a quantified representation of papillary muscles of the left ventricle;

determining a pattern of cardiac anatomy associated with the given individual based on (i) the quantified representation of the endocardial lumen of the left ventricle, (ii) the quantified representation of the myocardial wall of the left ventricle, and (iii) the quantified representation of the papillary muscles of the left ventricle;

defining at least one comparison technique between the pattern of cardiac anatomy associated with the given individual and at least one additional pattern of cardiac anatomy; and identifying the given individual based on the at least one defined comparison technique.

21. The system of claim 20, wherein the at least one processor is further operative for acquiring the multiple imaging modality signals pertaining to cardiac anatomy via at least one anatomical imaging modality including one of magnetic resonance imaging (MRI), computed tomography (CT), two-dimensional (2D) echo/ultrasound, three-dimensional (3D) echo/ultrasound, positron emission tomography (PET) or a combination thereof.

22. The system of claim 21, wherein the at least one processor is further operative for defining a similarity measure between the pattern of cardiac anatomy associated with the given individual and at least one additional quantified pattern of cardiac anatomy to produce at least one score.

23. The system of claim 22, wherein the at least one processor is further operative for geometric aligning and warping of the representations to be compared.

24. The system of claim 22, wherein the at least one processor is further operative for identifying individual papillary fibers and determining a correspondence between fibers in two representations.

* * * * *